United States Patent
Austin et al.

(10) Patent No.: US 9,226,705 B2
(45) Date of Patent: Jan. 5, 2016

(54) HUMAN PERFORMANCE ENHANCEMENT METHOD AND APPARATUS

(71) Applicants: David G. Austin, Columbus, OH (US); Sharon M. Austin, Columbus, OH (US)

(72) Inventors: David G. Austin, Columbus, OH (US); Sharon M. Austin, Columbus, OH (US)

(*) Notice: Subject to any disclaimer, the term of this patent is extended or adjusted under 35 U.S.C. 154(b) by 0 days.

(21) Appl. No.: 14/510,421

(22) Filed: Oct. 9, 2014

(65) Prior Publication Data
US 2015/0105641 A1 Apr. 16, 2015

Related U.S. Application Data

(60) Provisional application No. 61/889,766, filed on Oct. 11, 2013.

(51) Int. Cl.
| | |
|---|---|
| *A61B 5/0476* | (2006.01) |
| *A61B 5/145* | (2006.01) |
| *A61B 5/18* | (2006.01) |
| *A61B 5/00* | (2006.01) |

(Continued)

(52) U.S. Cl.
CPC ............... *A61B 5/18* (2013.01); *A61B 5/4809* (2013.01); *A61B 5/6891* (2013.01); *A61H 7/001* (2013.01); *A61H 23/04* (2013.01); *A61N 1/26* (2013.01); *A61N 1/322* (2013.01); *B60N 2/448* (2013.01); *A61B 5/021* (2013.01); *A61B 5/0476* (2013.01); *A61B 5/0488* (2013.01); *A61B 5/053* (2013.01); *A61B 5/11* (2013.01); *A61B 5/1135* (2013.01); *A61B 5/14542* (2013.01); *A61B 5/162* (2013.01); *A61B 5/6893* (2013.01); *A61H 2201/0138* (2013.01); *A61H 2201/0149* (2013.01); *A61H 2201/1623* (2013.01)

(58) Field of Classification Search
CPC .... A61B 5/02055; A61B 5/04; A61B 5/0006; A61B 5/6893; A61B 5/6887; A61B 5/18; A61B 5/165; A61B 5/0537; A47C 4/54
See application file for complete search history.

(56) References Cited

U.S. PATENT DOCUMENTS

| | | | |
|---|---|---|---|
| 3,613,671 A | * | 10/1971 | Poor et al. .................... 601/149 |
| 3,983,640 A | | 10/1976 | Cardullo et al. |

(Continued)

OTHER PUBLICATIONS

Douglas, N. et al. "Respiration during sleep in normal man"; Thorax 1982:37:840-844.*

(Continued)

*Primary Examiner* — William Thomson
*Assistant Examiner* — Marie Archer
(74) *Attorney, Agent, or Firm* — Frank H. Foster; Kremblas & Foster (57) ABSTRACT

A human body support, such as a chair, has a plurality of support segments that are arranged in an array. Each support segment has a protrusion elevation that is independently variable and controllable in its distance of protrusion elevation against the supported human body. A sensor is connected to a human body on the support and senses a human body parameter that can indicate the presence of drowsiness. A controller analyzes the sensed parameter to detect whether the sensed parameter is within a range indicating the presence of drowsiness. The controller applies a wave of varying segment protrusion elevation against the human body in response to the detection of drowsiness. The wave progresses in a direction from an inferior location on the human body toward a more superior location. Alternatively, a wave of electrical stimuli is applied by similarly positioned electrodes and causes periodic tightening and relaxing of proximate muscles.

18 Claims, 3 Drawing Sheets

(51) Int. Cl.
*A61H 7/00* (2006.01)
*A61H 23/04* (2006.01)
*A61N 1/26* (2006.01)
*A61N 1/32* (2006.01)
*B60N 2/44* (2006.01)
*A61B 5/021* (2006.01)
*A61B 5/053* (2006.01)
*A61B 5/16* (2006.01)
*A61B 5/0488* (2006.01)
*A61B 5/11* (2006.01)
*A61B 5/113* (2006.01)

(56) References Cited

U.S. PATENT DOCUMENTS

| | | | |
|---|---|---|---|
| 3,990,742 A | | 11/1976 | Glass et al. |
| 5,127,708 A | * | 7/1992 | Kishi et al. ................ 297/284.1 |
| 5,433,506 A | | 7/1995 | Jensen |
| 6,088,643 A | | 7/2000 | Long et al. |
| 7,727,171 B2 | | 6/2010 | Ozaki et al. |
| 8,011,044 B1 | | 9/2011 | Jones |
| 8,740,303 B2 | | 6/2014 | Halliday et al. |
| 2002/0183644 A1 | * | 12/2002 | Levendowski et al. ....... 600/544 |
| 2006/0049678 A1 | | 3/2006 | Kern et al. |
| 2007/0273188 A1 | | 11/2007 | Morrison |
| 2007/0273611 A1 | * | 11/2007 | Torch ................................ 345/8 |
| 2009/0027212 A1 | * | 1/2009 | Nakagoshi et al. ........... 340/575 |
| 2009/0099490 A1 | | 4/2009 | Durt et al. |
| 2012/0212353 A1 | * | 8/2012 | Fung et al. ................... 340/905 |

OTHER PUBLICATIONS

White, W. B "Importance of Blood Pressure Control Over a 24-Hour Period"; Supplement to Journal of Managed Care Pharmacy JMCP Oct. 2007 vol. 13, No. 8. S34-S39.*

* cited by examiner

HUMAN PERFORMANCE ENHANCEMENT METHOD AND APPARATUS

CROSS-REFERENCES TO RELATED APPLICATIONS

This application claims the benefit of U.S. Provisional Application No. 61/889,766 filed Oct. 11, 2013.

STATEMENT REGARDING FEDERALLY-SPONSORED RESEARCH AND DEVELOPMENT (Not Applicable)

THE NAMES OF THE PARTIES TO A JOINT RESEARCH AGREEMENT (Not Applicable)

REFERENCE TO AN APPENDIX (Not Applicable)

BACKGROUND OF THE INVENTION

This invention relates to a method and apparatus for improving and protecting the health and alertness, particularly cardiovascular and mental functions, of individuals who are engaged in reduced physical activity, particularly when seated. More particularly, the invention is directed to sensing the drowsiness of such individuals by sensing a parameter of the individual's body that, at known values of the parameter, indicates a drowsiness condition and then applying stimulations to the body of such individuals to counteract the drowsiness, particularly by reversing the pooling of blood in the lower extremities of the individual's body. The applied stimulations are in the form of a wave applied to the body of the individual. The wave progresses from a more inferior location on the individual toward a more superior position. The crests of the wave cause a compression or contraction of the individual's muscles which pushes blood from the lower extremities into the upper body.

When a person remains in a seated posture for a period of time, the person's venous blood shifts disproportionately away from the brain and into the lower extremities. This pooling of the blood in the legs results in a reduced blood flow to the brain which, in turn, causes drowsiness and reduced attentiveness. When a person is engaged in normal physical activity, such as walking or other physical exercise, the normal periodic contraction of the leg and other muscles assists in pumping the blood upwardly in the body away from the lower extremities. However, when a person is seated, the person is engaged in reduced muscle activity so the muscles, especially those in the lower extremities, are less often or never contracted. Consequently, while gravity continues to attract blood downward into the lower extremities, the muscles are not assisting in moving the blood upward in the body.

There are several undesirable consequences of this pooling of the blood in the lower extremities. One consequence is that a person driving an automobile or other vehicle or operating other machinery becomes drowsy, inattentive and less vigilant. All of these consequences have an obvious undesirable effect upon the person's ability to operate a vehicle or machinery in a safe manner. Unfortunately this problem sometimes leads to increased operator error, not only for persons operating machinery, but also for others such as persons sitting at and operating a computer or a student taking a test in school.

There are also additional long term health consequences that result from excessive occurrences and lengthy time intervals of such blood pooling.

For example, blood pooling in the lower extremities contributes significantly to sleep apnea because the blood pooling causes retained fluid. The sleep apnea itself contributes to further drowsiness and inattentiveness because it results in less effective rest. The retained fluid results in an exponential decrease of airflow with resultant disturbed sleep, increased risk of obstructive sleep apnea and cardiovascular sequelae. The disturbed sleep results in drowsy driving, operator error and an increased risk of vehicular accidents. Disrupted sleep can also lead to some form of Attention Deficit Disorder. A method and apparatus that would reduce the pooling of blood in the lower extremities, of for example a truck driver, would not only improve attentiveness by reducing drowsiness and increasing attentiveness during operation of the truck, but would also improve the quality of rest and the improved alertness gained from the better rest.

Another health consequence example is that blood pooling as a result of physical inactivity can contribute significantly to the development of varicose veins. Prolonged inactivity from sitting causes blood pressure to rise in the veins of the lower extremities. If the pressure rises above the structural limits of the veins, a likelihood that increases with age, the increased pressure causes stretching of the vessel walls (varicose veins). Simultaneously, fluid is expressed through the venous walls into the soft tissue of the legs resulting in fluid retention and edema It is therefore an object and feature of the invention to provide an apparatus and method for reducing the blood pooling while a person is seated and relatively inactive and thereby reducing the undesirable health and safety problems that blood pooling can cause. The invention is applicable to persons confined in a wheelchair, truck and motor vehicle drivers and occupants, aircraft pilots and occupants, heavy equipment operators, bedridden individuals, computer operators and students of all ages.

BRIEF SUMMARY OF THE INVENTION

The invention utilizes a human body support, such as a chair, that has a plurality of support segments that are arranged in an array. Each support segment has a protrusion elevation that is independently variable and controllable in its distance of protrusion elevation against the supported human body. A sensor that is connected to or receives images from a human body on the support senses a human body parameter that is capable of indicating the presence of drowsiness in the human body. A controller analyzes the sensed parameter to detect whether the sensed parameter is within a range indicating the presence of drowsiness. The controller applies a wave of varying segment protrusion elevation against the human body in response to the detection of drowsiness. The wave progresses in a direction from an inferior location on the human body toward a more superior location.

Another embodiment of the invention supports the human body on a support having a plurality of electrodes that are arranged in an array. The array extends from an inferior position to a more superior position along the supported human body. As with the first embodiment, a measurable parameter of the human body is sensed. The parameter is capable of indicating the presence of drowsiness in the human body. Also as with the first embodiment, a controller detects whether the sensed parameter is within a range indicating the presence of drowsiness. However, with this second embodiment, a wave of electrical stimuli is applied against the human body in response to detection of a sensed parameter within the drowsiness range. The electrical stimuli cause periodic tightening and relaxing of the muscles and progresses in a direction from an inferior location on the human body toward a more superior location.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

U.S. Provisional Application No. 61/889,766 filed Oct. 11, 2013 is incorporated by reference into this application.

Figure 1:
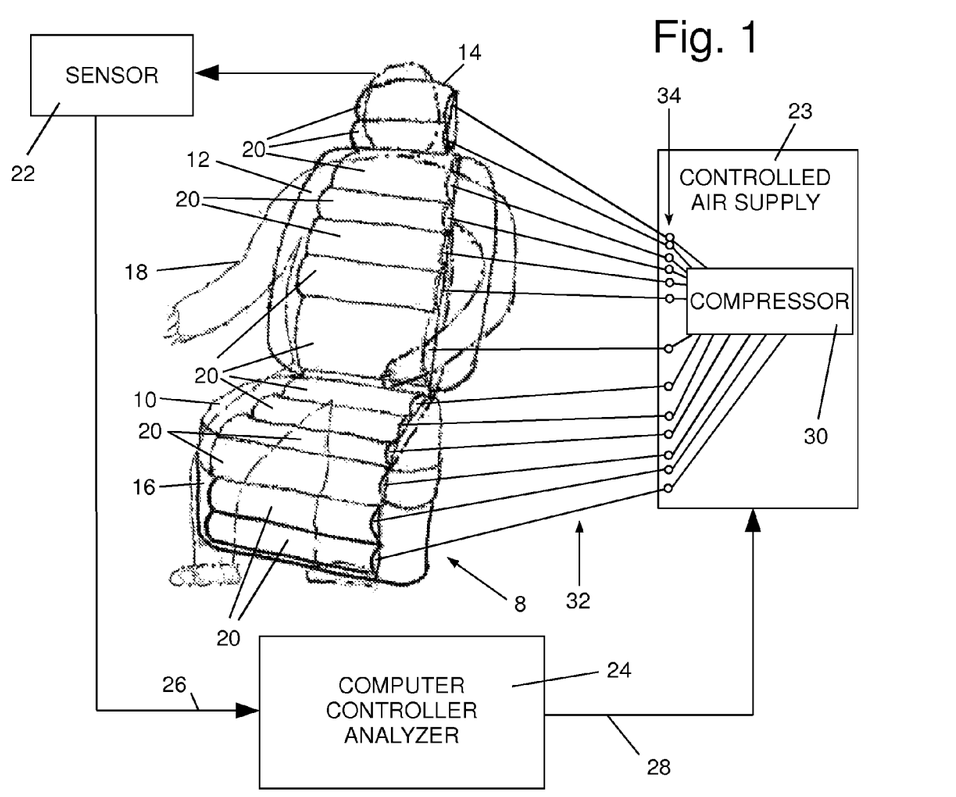
FIG. 1 is a diagrammatic view of the preferred embodiment of the invention

FIG. 1 illustrates an embodiment of the invention for improving and protecting the cardiovascular and mental functions of a human who is seated and engaged in reduced physical activity. The embodiment has a human body support in the form of a chair 8 constructed with chair components that comprise a seat 10, a seat back 12, a headrest 14 and a seat front 16. The seat front 16 is illustrated in a vertical orientation although alternatively it can be inclined downward and away from the chair 8 so that it provides more substantial support for the legs. A human body 18 (illustrated in a phantom outline) is supported in the seat 10 in the conventional seated posture.

Positioned on all the chair components are a plurality of support segments 20. The support segments 20 are arranged in an array or matrix that is distributed across the chair components in locations for engaging the seated human body 18. Each support segment 20 is capable of being controllably, selectively and independently varied in its elevation distance so that its distance of protrusion against the supported human body can be independently increased or decreased. The support segments 20 extend laterally with respect to the human body 18 and are positioned at side by side intervals from a more inferior position to a more superior position along the chair 8 components and beneath the supported human body 18. Preferably the support segments 20 are distributed longitudinally all the way from the ankles to the neck of the supported body 20. The array of support segments 20 can, of course, be distributed over less than all the way from the ankles to the neck with some proportional reduction of effectiveness. The support segments 20 that are illustrated in FIG. 1 are contiguous in the longitudinal direction with each support segment 20 being a single support segment 20 extending laterally across the chair. Alternatively, the support segment can be spaced apart longitudinally. As a further alternative, each lateral support segment can comprise a laterally arranged series of support segments that are either contiguous or laterally spaced apart. As will be described below, the preferred support segments 20 are inflatable air compartments with chambers which can be selectively and independently increased or decreased in their inflation pressure. Each preferred support segment 20 is connected to a controlled air supply 23 that is further described below.

A sensor 22 is mounted to the human body 18 for measuring a parameter of the human body 18 that is capable of indicating the presence of drowsiness in the human body 18. There are multiple different kinds of sensors that can be used as alternatives or in combination. These are discussed below and include an electroencephalograph (EEG) that monitors the brain's spontaneous electrical activity.

A controller 24 analyzes the analog or digital data signal from the sensor 22 and controls the protrusion elevation, such as by inflation and deflation, of each of the support segments 20 in response to its programmed analysis and control algorithm. Preferably, controller 24 is one of the many types of digital computing devices, such as a microcontroller, microprocessor or digital signal processor. The controller 24 has an input 26 connected to the output of the sensor 22 for receiving a signal representing the sensed parameter. The controller also has an output 28, which may be a data bus, that sends control data to control the distance of protrusion elevation of each of the support segments 20. The controller analyzes the signal from the sensor 22 to detect whether the sensed parameter is within a range indicating the presence of drowsiness. Upon detection of drowsiness, the controller applies a wave of varying segment protrusion elevation against the human body 18 in response to detection of a sensed parameter within that range. The wave progresses in a direction from a more inferior location on the human body toward a more superior location.

In the preferred embodiment, each of the support segments 20 is a sealed compartment having a chamber that is inflatable with a fluid independently of the other compartments. The chambers are inflated or deflated by the controlled fluid supply 23 which is controlled by the controller 24. Although the fluid can be a liquid or a gas, the preferred fluid is air so the preferred controlled fluid supply is a controlled air supply 23. The controlled air supply 23 includes an air compressor 30. It also has a multiplicity of fluid conduits 32, each of which makes a separate and discrete fluid connection from the fluid supply 23 to, and associated with, each of the support segment chambers. The controlled air supply 23 also has a multiplicity of valves 34 with a different one of the valves associated with each conduit 32. Each valve is connected between its associated conduit and the air compressor 30. Each valve has at least two and preferably three positions. One position opens a fluid conducting path from the compressor to the conduit associated with the valve for inflating its associated support segment, one position opens a path from its associated fluid conduit to the atmosphere for deflating its associated support segment, and preferably a third position closes any connection to its associated conduit for maintaining an inflation pressure. Each of the valves is actuable to each of its three positions by a signal from the controller 24. This arrangement permits the controller 24 to selectively initiate, independently for each support segment, the addition or the escape of fluid from the chamber of each support segment 20.

This arrangement can also include pressure sensors in each support segment chamber that communicate pressure information to the controller 24 so that traditional feedback control principles can be applied for maintaining or controlling the pressure in each chamber according to preselected pressure or force sequences that generate the wave. Alternatively, the forces applied by the support segments to points on a person's body can be detected by an array, for example a 10 by 20 matrix of ultrathin flexible force sensing sensors, that together form a biomedical pressure monitor available from Universal Cement Corporation and sold under the trademark Uneo™. The force signals from the force sensors of the array can also be used in a traditional feedback control system for monitoring and controlling the force applied by the support segments to generate the wave.

The prior art has described other structures for seats with multiple individual support segments that are controlled by a computer-based controller. Such support systems are shown, for example, in U.S. Pat. Nos. 3,983,640 and 6,088,643 and U.S. Publ 2006/0049678 all of which are herein incorporated by reference. There are many possible structural variations. For example, the preferred embodiment illustrated in FIG. 1 has an array with a single column of multiple support segments with a single support segment in each row that extends laterally across the chair.

Figure 2:
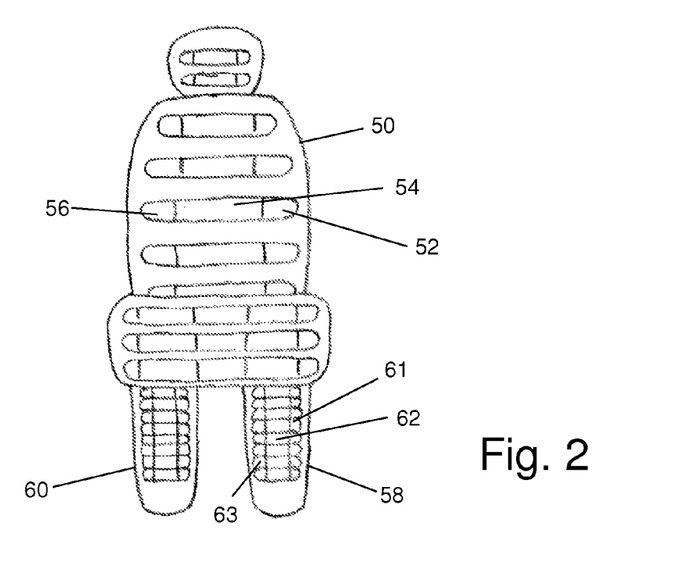
FIG. 2 is an illustration of an alternative embodiment of the invention.

Alternatively, each row can comprise multiple support segments as illustrated in FIG. 2. For example, referring to FIG. 2, on the chair 50 each row has three columns 52, 54 and 56 of support segments which can be independently controlled. Additionally, because application of the wave along the lower extremities where the blood pools is of major importance, the leg support portion of the chair can be bifurcated into two separate leg supports 58 and 60. Each of these leg supports 58 and 60 has three columns of support segments such as 61, 62 and 63 on leg support 58. This construction allows the wave to be applied beginning at or near the ankles so that the entire calf is stimulated by the wave for maximum effectiveness in reversing the pooling of blood in the lower extremities.

The support segments have been illustrated as built into or attached to a chair. However, alternatively, the support segments can be formed into or mounted to a garment so that they are worn on the body. In that case it is possible that the support segments entirely surround the body, or part of the body, such as the lower limbs. As a further alternative, the support segments can be formed as or mounted to a sheet or blanket so they can be carried by hand and placed on a surface to cover existing chairs, wheelchairs, a bed or other human support. These alternatives provide multi-use and ease of portability.

Sensors and Sensed Parameter Alternatives

An important feature of the invention is that the condition of drowsiness is continuously monitored and automatically sensed rather than relying on manual initiation of the wave by a person. This feature avoids the problem resulting from the probability that a person who has become drowsy will not be aware of becoming drowsy. The prior art has described many various types of drowsiness sensors, several of which are commercially available. These sensors and the parameters that they sense may be used for sensing drowsiness with the present invention along with their associated computing and analysis hardware and software. Many have been developed by automobile manufacturers and several are listed on Wikipedia under the heading Driver Drowsiness Detection. Information and sellers of this equipment may be found by an internet search, such as for the keywords "drowsiness sensor". However, these prior art devices only provide a signal or alarm to alert the driver to his or her drowsiness condition.

The commercially available equipment measures a parameter and includes a parameter range that is indicative of the presence of drowsiness. For different parameters, the range of parameter values that indicate drowsiness can be less than, greater than or equal to a value, depending upon the particular parameter being measured. If desired, more than one sensor to detect more than one parameter may be used in combination to detect drowsiness.

The following are some examples of sensor equipment and sensed parameters, each of which may be used in addition to or as alternatives to others. They use different combinations of sensors and/or camera in a headrest, visor, seatbelt, seat or steering wheel. Each device has software that initially acquires the user's physiological values of one or more sensed parameters. After acquisition of normal values, software computation will look for a statistical variance and trigger an alarm that is used to initiate the wave that is applied to the person's body. This alarm may also be simultaneously sent to other locations, such as a trucking firm's headquarters.

A preferred sensor and sensing method uses the principles of electroencephalography (EEG). Electroencephalography is used to sense and record electrical activity along the scalp. EEG measures voltage fluctuations resulting from ionic current flows within the neurons of the brain. In clinical contexts, EEG refers to the recording of the brain's spontaneous electrical activity as recorded from multiple electrodes placed on the scalp. Diagnostic applications generally focus on the spectral content of EEG. Equipment for sensing EEG and EKG parameters is available commercially from Sleepmate Products.

In the preferred embodiment, the sensor is an electroencephalograph and its associated electrodes. The EEG electrodes may be mounted in a cap, hat, headband or other object that fits comfortably on the head of a person. The electrodes are arranged so that they contact the scalp of the person seated on the support segments. The electroencephalograph detects electrical impulses in the brain and generates an electroencephalogram in the form of an electrical analog or digital signal that is applied to the controller 24. The controller 24 has a stored programmed algorithm, such as a fast Fourier transform, that detects the fundamental frequency of the electroencephalogram. The algorithm then detects whether the fundamental frequency of the electroencephalogram is less than 20 Hz. If the fundamental frequency is less than 20 Hz, the controller applies the wave to the human body, by controlling the valves 34 in the case of the preferred embodiment illustrated in FIG. 1.

Respiration is an indicator of the state of alertness or drowsiness of a human. One known parameter for measuring respiration is tidal volume of airflow in units of my (mean ventilation). A sensor and its associated equipment of the type already known in the prior art medical field can be used and its output connected to the controller of the invention. A sensor may also be constructed by mounting a force or pressure sensor between the torso and a band that surrounds the torso, such as a pants belt. As a portion of the torso expands and contracts during respiration, the force against the sensor will vary by increasing in proportion to inspiration and decreasing in proportion to expiration. Consequently, the difference between the minimum force and the maximum force is a measure of tidal volume of airflow because the force difference is proportional to the tidal volume. The analysis of that force parameter computes that difference whenever the operation of an embodiment of the invention is initiated. That force difference is then periodically measured during operation of the embodiment. A decrease of tidal volume of airflow (e.g. a decrease of the above difference in the force or pressure applied to the above-described sensor) to below 85% of its initial value is believed to indicate the presence of sufficient drowsiness to justify the application of the wave to the human body.

A piezoelectric respiratory belt transducer is a commercially available monitor that contains a piezo-electric device that responds linearly to changes in length. It measures changes in thoracic or abdominal circumference during respiration. These measurements can indicate inhalation, expiration and breathing strength and can be used to derive breathing rate. Another commercially available device is a respiratory inductance plethysmography (RIP) belt that evaluates pulmonary ventilation by measuring the movement of the chest and abdominal wall. A reduction in inhalation in the range of at least 10% to 20% can be considered an indication of drowsiness and preferably a reduction of at least 15% is considered an indication of drowsiness with the invention.

A reduction in blood pressure is another indicator of drowsiness. There are several blood pressure detectors for measuring human blood pressure and these can be used to supply blood pressure data to the controller of the invention as a measureable parameter that indicates the presence of drowsiness. The blood pressure is measured whenever the operation of an embodiment of the invention is initiated. The blood pressure is subsequently periodically measured during operation of the embodiment. While a 20% decrease in blood pressure indicates the likely presence of drowsiness and that value can be used, it is preferable that the controller initiate the wave upon detection of a decrease of 10% or more.

Photoplethysmography (PPG) is a simple and low-cost optical technique that has been used commercially to detect blood volume changes in the microvascular bed of tissue. It is desirable for use with the present invention because it can be used non-invasively to make measurements at the skin surface, such as the surface of a toe, and can be used to measure blood pressure.

Oximetry offers another alternative parameter that can be sensed as an indicator of drowsiness. Oximetry uses an oximeter to measure the oxygen content of the blood (oxyhemoglobin). The medical field prior art provides sensors and associated equipment that measures oxyhemoglobin and these devices can be used in the present invention. For example, the prior art shows sensors that are attached to an ear lobe but similar sensors can be mounted to a cap, hat or headband so the sensor is retained against the skin of the user. A 3% drop or desaturation of oxyhemoglobin is believed to be a sufficient indicator of drowsiness that the application of the waves to the human body should be initiated for that amount or more of a decrease.

Another example of a measureable parameter that indicates the presence of drowsiness in the human body is fluid retention in the legs. The prior art has developed a bioelectric impedance analysis that is capable of determining the leg fluid volume (LGF). This technology measures the bioelectric impedance at the surface of the human leg and computes the leg fluid retention in mL (milliliters) per leg. As explained above, as a person sits and remains relatively inactive, the fluid content in the legs increases. An increase of fluid volume above 100 mL per leg is believed to indicate a sufficient state of drowsiness and/or inactivity to merit initiating the application of the waves to the human body.

Yet another example of a measureable parameter that indicates the presence of drowsiness in the human body is the percentage of closure of a person's eyelids. Existing electrooculography (EOG) equipment is available for measuring percentage of closure. The most appropriate equipment for use with the invention uses an ocular video camera that can be mounted in a variety of locations, such as on a computer monitor and directed toward the computer user, on a vehicle visor or dashboard, on a cap or on eyeglasses. The camera records ocular activity and transmits the data to a controller, such as a computer or other digital data processor, which is programmed to detect and record eyelid status and compute the percentage of closure. Equipment and its software for measuring percentage of closure is commercially available. Typically, a person is considered drowsy if the percentage of time that the person's eyelids are 80% or more closed exceeds 0.5% over a 1 minute time interval. However, in embodiments of the invention, it is preferred that application of the wave to the human body is initiated if the percentage of time that the person's eyelids are 80% or more closed exceeds 0.25%.

Still another example of a measureable parameter that indicates the presence of drowsiness in the human body is psychomotor vigilance performance measured by commercially available equipment for a psychomotor vigilance test (PVT). Commercially available equipment, sold by Joggle Research, measures reaction time by the human subject and is claimed to be 98% to 100% accurate. This equipment tests the reaction time of the human subject to a light stimulus, such as a flash, during a 3 minute period. An average reaction time of greater than 500 milliseconds is considered drowsy. However, for the present invention, a reaction time that exceeds 250 milliseconds is a preferred indication of drowsiness. With PVT, if the user tested positive for drowsiness, the blood flow return waves of the invention would be initiated and run continuously.

Another example of a measureable parameter that indicates the presence of drowsiness in the human body is head droop. When a person becomes drowsy, it is common for the neck to bend and allow the head to droop downward toward the person's chest. A 3-D video camera or 3-D sensor or scanner, such as those used commercially for sensing the distance to points on an object for creating a 3-D digital model of an object, can be used to monitor a person's head position. The sensor can be mounted in a headrest of a chair, on a vehicle visor or on a computer monitor.

Electromyography [EMG] uses an instrument called an electromyograph to produce a record called an electromyogram. Electrodes are placed in contact with the skin and, during use, the electrodes deliver electrical nerve stimuli. A programmable multi-channel controller modulates the electrical current's intensity (voltage/amperage) [and can also vary frequency and duration] for motor nerve stimulation. EMG signals are essentially made up of superimposed motor unit action potentials (MUAPs) from several motor units. For a thorough analysis, the measured EMG signals can be decomposed into their constituent MUAPs. MUAPs from different motor units tend to have different characteristic shapes, while MUAPs recorded by the same electrode from the same motor unit are typically similar. Notably MUAP size and shape depend on where the electrode is located with respect to the fibers and so can appear to be different if the electrode moves position. EMG decomposition is non-trivial, although many methods have been proposed.

Rectification is the translation of the raw EMG signal to a single polarity frequency (usually positive). The purpose of rectifying a signal is to ensure the raw signal does not average zero, due to the raw EMG signal having positive and negative components. It facilitates the signals and process and calculates the mean, integration and the fast fourier transform (FFT). The two types of rectification of signals refer to what happens to the EMG wave when it is processed. These types include full length frequency and half length. Full length frequency adds the EMG signal below the baseline (usually negative polarity) to the signal above the baseline making a conditioned signal that is all positive. This is the preferred method of rectification because it conserves all signal energy for analysis, usually in the positive polarity. Half length rectification deletes the EMG signal below the baseline. In doing so, the average of the data is no longer zero therefore it can be used in statistical analyses. The only difference between the two types of rectification is that full-wave rectification takes the absolute value of the signal array of data points.

Of course there are other known parameters of drowsiness exhibited by the human body that can be quantitatively measured and analyzed to make an assessment of a state of a person's drowsiness.

Wave of Electrical Stimuli

Figure 3:
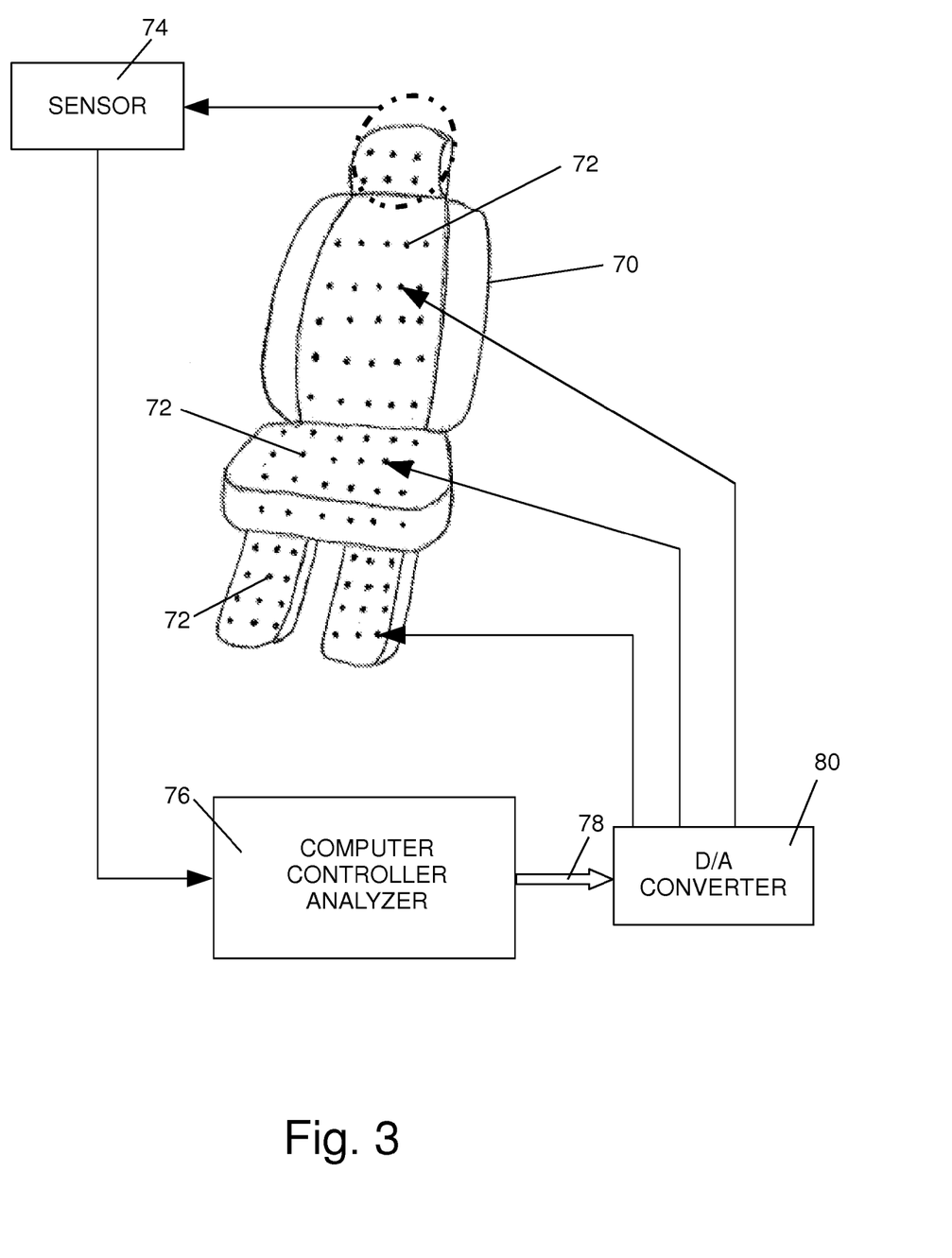
FIG. 3 is a diagrammatic view of yet another alternative embodiment of the invention.

FIG. 3 illustrates an alternative embodiment of the invention for applying a wave to the human body in order to reverse blood pooling in the lower extremities. A chair 70 has a plurality of electrodes 72 that are arranged in an array or matrix. The electrodes 72 are illustrated as dots and a reference numeral is applied only to some representative electrodes to avoid excessive clutter on the drawing. The electrodes are spaced laterally and longitudinally in the array with respect to the human body. The array of electrodes 72 extends longitudinally from an inferior position to a more superior position along a supported human body.

As with the embodiment of FIG. 1, a sensor 74 is provided for connection to the supported body and measures a parameter of the human body that is capable of indicating the presence of drowsiness in the human body. The sensor can be any of the sensors described above.

A controller 76 has an input connected to the sensor for receiving a signal representing the sensed parameter as with the embodiment of FIG. 1. The controller has outputs, illustrated as an output bus 78 that are connected through a digital to analog converter 80 to each of the electrodes 72. The controller 76 detects whether the sensed parameter is within a range indicating the presence of drowsiness as with the embodiment of FIG. 1. However, in this embodiment the controller 76 applies a wave of electrical stimuli against the human body in response to detection of a sensed parameter within the drowsiness range. The electrical stimuli have a voltage and current that are sufficient to cause tightening of muscles that are proximate to the electrodes. The electrical stimuli are pulses separated by a time interval that allows relaxation of the proximate muscles. The periodic pulses of the wave are phased so that a wave of electrical stimuli progresses in a direction from an inferior location on the human body toward a more superior location. The wave of electrical stimuli cause a wave of tightened muscles to progress along the body in the upward direction causing the pooled blood to be pumped upwardly in the body in a manner that is analogous to the natural tightening of muscles. This neurostimulation, sequentially increases muscle tonus to reproduce a muscle action similar to walking.

Electrical stimulation can be applied using transcutaneous electrical nerve stimulation. Typically the stimulation is applied at a frequency of 1 to 4 Hz with a pulse duration of 100 to 250 microseconds and a current of 30 to 50 milliamps. This produces strong rhythmic muscle contractions.

The electrodes can, like the support segments illustrated in FIGS. 1 and 2, be mounted within a garment or on a sheet as described above. In that case the electrodes can surround human body parts, particularly the lower limbs.

In addition to the application of a wave to the human body by means of support segments that are inflatable with a fluid, the support segments can also be in the form of an array of solid segments that are mechanically lifted by cams or connecting rods and crank shaft arrangements. U.S. Pat. No. 8,011,044, which is herein incorporated by reference, illustrates a wheel chair with such an arrangement. In such an embodiment, the crank or cams of each row of solid support segments are individually controlled by the controller to generate the wave that progresses from a lower to a more superior location along the human body.

Figure 4:
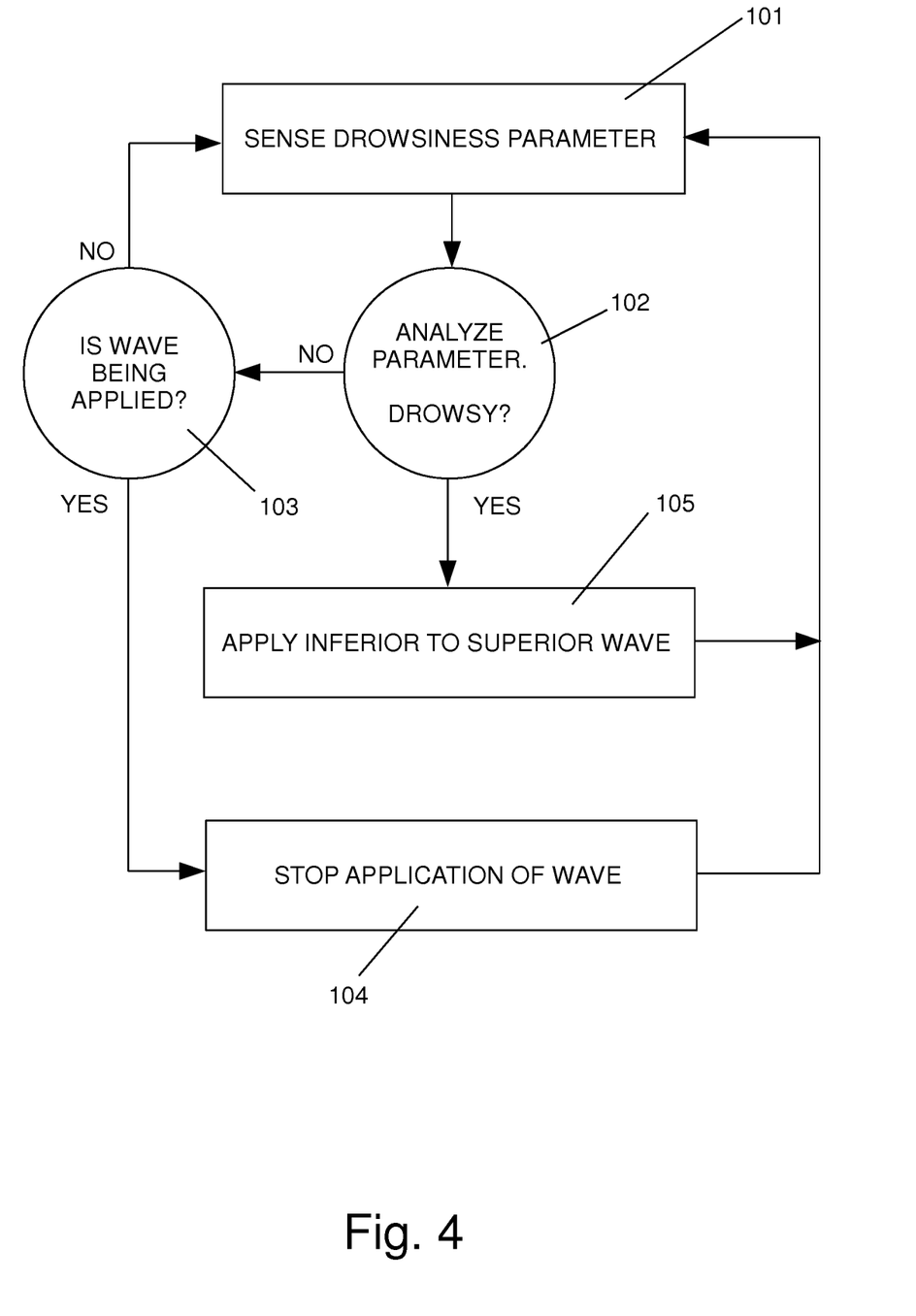
FIG. 4 is a flow chart illustrating the method of the invention.

The operation of embodiments of the invention is illustrated in FIG. 4. The human body is supported either on the plurality of support segments such as those shown in FIGS. 1 and 2 or on the electrodes illustrated in FIG. 3. Referring to FIG. 4, at step 101 the controller inputs the drowsiness parameter that is capable of indicating the presence of drowsiness in the human body. At step 102, the controller analyzes the drowsiness parameter to detect whether the sensed parameter is within a range indicating the presence of drowsiness.

If the analysis at step 102 indicates NO, the person is not drowsy, then at step 103 the controller determines whether a wave is already being applied by the chair support segments or electrodes to the human body. If that determination is NO a wave is not being applied, the program returns to inputting the sensed parameter at step 101 and continues around that loop so long as drowsiness is not detected. If at step 103 the controller determines that YES a wave is being applied to the human body, the controller progresses to step 104 and stops the application of the wave because there is no longer a drowsy condition. Alternatively, a time delay interval can be inserted by recording the amount of time that there is an absence of drowsiness and allowing application of the wave to the human body for a selected extended time interval. This allows the waves to continue to be applied after drowsiness has ceased in order to maintain the more alert condition. A manual deactivation of the application of the wave can additionally be inserted to allow the person being monitored to manually discontinue the application of the waves. After stopping the application of the wave to the person at step 104, the program returns to step 101 and inputting the drowsiness parameter.

If at step 102 the analysis of the drowsiness parameter indicates YES the person is drowsy, then the program proceeds to step 105 and initiates the application of the wave to the human body.

Wave Characteristics

Most preferably, the wave is applied beginning from immediately at or slightly above the ankles of the human body. From there it progresses sequentially upward across the leg calf, thighs, hips and buttocks, low back, torso, and at least to the neck. The frequency of the wave preferably mimics slow walking but may be adjusted depending on sensor array readouts, user performance and comfort preference. Because slow walking is approximately 90 steps per minute, the typical ideal frequency is approximately 1.5 Hz. However, the preferred frequency of the wave is in the range of 1 to 2 Hz to allow for variations in individuals and other factors.

The wave varying segment protrusion elevation or the wave of electrical stimuli can have several different waveforms. For example, the wave can be a series or sequence of pulses each having a single selected amplitude of protrusion distance or electrode voltage and current but separated by interposed intervals of zero protrusion distance or electrode voltage and current. Alternatively, the wave can be sinusoidal, with the distance of protrusion or electrode voltage and current periodically or repetitively increasing in increments and then decreasing in increments. Of course other waveforms can be generated.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The following claims were deleted from this application as prepared in order to meet the 30 claim maximum for requesting expedited examination. They are placed here in the specification to avoid any new matter objections in the event that they are inserted in any subsequent application. This should be deleted upon allowance.

31. An apparatus in accordance with claim 27 wherein the sensor comprises a blood pressure detector.
32. An apparatus in accordance with claim 27 wherein the sensor comprises a bioelectric impedance analyzer that detects fluid retention in legs by bioelectric impedance analysis.
33. An apparatus in accordance with claim 27 wherein the sensor comprises an electrooculograph.

The invention claimed is:

1. A method for improving and protecting the cardiovascular and mental functions of a human who is seated and engaged in reduced physical activity, the method comprising:
    (a) supporting a human body on a support having a plurality of support segments that are arranged in an array, each support segment having an independently variable and controllable distance of protrusion elevation against the supported body, the support segments extending laterally with respect to the human body and positioned side by side from an inferior position to a more superior position along the supported human body;
    (b) sensing a measurable parameter of the human body, the parameter being capable of indicating the presence of drowsiness in the human body;
    (c) detecting whether the sensed parameter is within a range indicating the presence of drowsiness; and
    (d) applying a wave of varying segment protrusion elevation against the human body in response to detection of a sensed parameter within said range, the wave progressing in a direction from an inferior location on the human body toward a more superior location
wherein the sensing step comprises detecting an initially sensed value of fluid retention in the legs by bioelectric impedance analysis and wherein the step of detecting whether the sensed parameter is within a range indicating the presence of drowsiness comprises detecting whether there has been an increase of fluid volume of 100 mL per leg or more above the initially sensed value of fluid volume per leg and the step of applying the wave is performed if there has been an increase of fluid volume of 100 mL per leg or more above the initially sensed value.

2. An apparatus for improving and protecting the cardiovascular and mental functions of a human who is seated and engaged in reduced physical activity, the apparatus comprising:
    (a) a human body support having a conventional seated posture for a human body, the support having a plurality of support segments that are arranged in an array, each support segment having an independently variable and controllable distance of protrusion elevation against the supported body, the support segments extending laterally with respect to the conventional seated posture of a human body and positioned side by side from an inferior position to a more superior position along the conventional seated posture of a supported human body;
    (b) a sensor measuring a parameter of the human body that is capable of indicating the presence of drowsiness in the human body; and
    (c) a controller having an input connected to the sensor for receiving a signal representing the sensed parameter and having outputs connected to each of the support segments, the controller detecting whether the sensed parameter is within a range indicating the presence of drowsiness and applying a wave of varying segment protrusion elevation against the human body in response to detection of a sensed parameter within said range, the wave progressing in a direction from an inferior location on the human body toward a more superior location
wherein the sensor comprises a bioelectric impedance analyzer that detects fluid retention in legs by bioelectric impedance analysis.

3. A method for improving and protecting the cardiovascular and mental functions of a human who is seated and engaged in reduced physical activity, the method comprising:
    (a) supporting a human body on a support having a plurality of support segments that are arranged in an array, each support segment having an independently variable and controllable distance of protrusion elevation against the supported body, the support segments extending laterally with respect to the human body and positioned side by side from an inferior position to a more superior position along the supported human body;
    (b) sensing a measurable parameter of the human body, the parameter being capable of indicating the presence of drowsiness in the human body;
    (c) detecting whether the sensed parameter is within a range indicating the presence of drowsiness; and
    (d) applying a wave of varying segment protrusion elevation against the human body in response to detection of a sensed parameter within said range, the wave progressing in a direction from an inferior location on the human body toward a more superior location
wherein the step of applying a wave further includes beginning the wave at the ankles and progressing along the calf of the human body.

4. A method in accordance with claim 3 wherein the sensing step comprises detecting electrical impulses in the human body's brain to obtain a signal representing an electroencephalogram and detecting the fundamental frequency of the electroencephalogram, and wherein the step of detecting whether the sensed parameter is within a range indicating the presence of drowsiness comprises detecting whether the fundamental frequency is less than 20 Hertz and the step of applying the wave is performed if the detected fundamental frequency is less than 20 Hertz.

5. A method in accordance with claim 3 wherein the sensing step comprises detecting an initially sensed value of tidal volume of airflow and wherein the step of detecting whether the sensed parameter is within a range indicating the presence of drowsiness comprises detecting whether there has been a decrease of tidal volume of airflow below 85% of the initially sensed value of tidal volume of airflow and the step of applying the wave is performed if the detected tidal volume of airflow is below 85% of the initially sensed value.

6. A method in accordance with claim 3 wherein the sensing step comprises detecting an initially sensed value of oxyhemoglobin and wherein the step of detecting whether the sensed parameter is within a range indicating the presence of drowsiness comprises detecting whether there has been a reduction or desaturation of oxyhemoglobin of 3% or more below the initially sensed value of oxyhemoglobin and the step of applying the wave is performed if there has been a reduction or desaturation of oxyhemoglobin of 3% or more below the initially sensed value.

7. A method in accordance with claim 3 wherein the sensing step comprises detecting an initially sensed value of blood pressure and wherein the step of detecting whether the sensed parameter is within a range indicating the presence of drowsiness comprises detecting whether there has been a reduction of blood pressure of 10% or more below the initially sensed value of blood pressure and the step of applying the wave is performed if there has been a reduction of blood pressure of 10% or more below the initially sensed value.

8. A method in accordance with claim 3 wherein the sensing step comprises detecting the percentage of time that the person's eyelids are 80% or more closed and wherein the step of detecting whether the sensed parameter is within a range indicating the presence of drowsiness comprises detecting whether the percentage of time that the person's eyelids are 80% or more closed exceeds 0.5% and the step of applying the wave is performed if the percentage of time that the person's eyelids are 80% or more closed exceeds 0.5%.

9. A method in accordance with claim 3 wherein the sensing step comprises testing the reaction time of the human body to a light stimulus and wherein the step of detecting whether the sensed parameter is within a range indicating the presence of drowsiness comprises detecting whether the reaction time exceeds an average of 250 milliseconds and the step of applying the wave is performed if the reaction time exceeds an average of 250 milliseconds.

10. An apparatus for improving and protecting the cardiovascular and mental functions of a human who is seated and engaged in reduced physical activity, the apparatus comprising:
(a) a human body support having a conventional seated posture for a human body, the support having a plurality of support segments that are arranged in an array, each support segment having an independently variable and controllable distance of protrusion elevation against the supported body, the support segments extending laterally with respect to the conventional seated posture of a human body and positioned side by side from an inferior position to a more superior position along the conventional seated posture of a supported human body;
(b) a sensor measuring a parameter of the human body that is capable of indicating the presence of drowsiness in the human body; and
(c) a controller having an input connected to the sensor for receiving a signal representing the sensed parameter and having outputs connected to each of the support segments, the controller detecting whether the sensed parameter is within a range indicating the presence of drowsiness and applying a wave of varying segment protrusion elevation against the human body in response to detection of a sensed parameter within said range, the wave progressing in a direction from an inferior location on the human body toward a more superior location
wherein the human body support includes a calf support and the array includes support segments mounted on the calf support.

11. An apparatus in accordance with claim 10 wherein the sensor comprises an electrooculograph.

12. An apparatus in accordance with claim 11, wherein the sensor comprises an electroencephalograph and its associated electrodes for mounting against the head of the supported body, the electroencephalograph detecting electrical impulses in the human body's brain to obtain a signal representing an electroencephalogram, the controller having a stored algorithm that detects the fundamental frequency of the electroencephalogram, and detects whether the fundamental frequency of the electroencephalogram is less than 20 Hertz and applies the wave if the detected fundamental frequency is less than 20 Hertz.

13. An apparatus in accordance with claim 11 wherein each of the support segments is an air compartment having a chamber that is inflatable with a fluid independently of the other compartments, and wherein the apparatus further comprises a controlled fluid supply and a fluid conduit connected from the fluid supply to and associated with each of the chambers, each fluid conduit including controllable valves for selectively permitting the addition or the escape of fluid from its associated chamber.

14. An apparatus in accordance with claim 11, wherein the fluid supply is an air compressor.

15. An apparatus in accordance with claim 11 wherein the sensor comprises an electroencephalograph.

16. An apparatus in accordance with claim 11 wherein the sensor comprises tidal volume of airflow detector.

17. An apparatus in accordance with claim 11 wherein the sensor comprises an oximeter.

18. An apparatus in accordance with claim 11 wherein the sensor comprises a blood pressure detector.

* * * * *